(12) United States Patent
Costabile (10) Patent No.: US 9,271,770 B2
(45) Date of Patent: Mar. 1, 2016

(54) BONE FIXATION SYSTEMS AND METHODS (75) Inventor: Jonathan T. Costabile, San Diego, CA (US)

(73) Assignee: ALPHATEC SPINE, INC, Carlsbad, CA (US)

( * ) Notice: Subject to any disclaimer, the term of this patent is extended or adjusted under 35 U.S.C. 154(b) by 1037 days.

(21) Appl. No.: 13/010,392

(22) Filed: Jan. 20, 2011

(65) Prior Publication Data
US 2012/0191141 A1   Jul. 26, 2012

(51) Int. Cl.
A61B 17/80   (2006.01)
A61B 17/70   (2006.01)

(52) U.S. Cl.
CPC ......... *A61B 17/8042* (2013.01); *A61B 17/7059* (2013.01)

(58) Field of Classification Search
CPC . A61B 17/80; A61B 17/8047; A61B 17/8033
USPC .................. 606/295, 280, 286, 289, 290, 296
See application file for complete search history.

(56) References Cited

U.S. PATENT DOCUMENTS

2005/0021032 A1*  1/2005  Koo .............................. 606/69
2008/0021476 A1*  1/2008  Kirschman .................... 606/69

* cited by examiner

*Primary Examiner* — David Isabella
*Assistant Examiner* — Christine Nelson
(74) *Attorney, Agent, or Firm* — John Chau (57) ABSTRACT A bone fixation plate includes a first opening formed in a plate that is configured to receive a first fastener; a second opening formed in the plate that is configured to receives a second fastener, and a retention member that extends into a third opening formed in the plate between the first opening and the second opening, wherein the retention member is elastically deformable between at least three positions.

12 Claims, 7 Drawing Sheets

BONE FIXATION SYSTEMS AND METHODS

FIELD

The present disclosure generally relates to the field of spinal orthopedics, and more particularly to methods and systems for bone fixation plates for vertebrae.

BACKGROUND

The spine is a flexible column formed of a plurality of bones called vertebrae. The vertebrae include a hollow cavity and essentially stack one upon the other, forming a strong column for support of the cranium and trunk of the body. The hollow core of the spine houses and protects the nerves of the spinal cord. The different vertebrae are connected to one another by means of articular processes and intervertebral, fibrocartilaginous bodies. The intervertebral bodies are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and consequently irritated. The result may be chronic and/or debilitating back pain due to these spinal disorders.

One procedure for treating spinal disorders involves using substantially rigid plates to hold vertebrae in desired spatial relationships and orientations relative to each other. During the procedure, the spine can be approached anteriorly or posteriorly. In either case, holes are drilled and tapped in at least two of the vertebrae, to receive screws or other fasteners used to secure the plate. The holes are accurately positioned with reference to openings formed through the plate. In some cases the screws may be self-tapping. Typically the plate is curved about its longitudinal axis to facilitate contiguous surface engagement of the plate with the vertebrae. With the plate maintained against the vertebrae, the fasteners are secured within the holes. As a result, the plate maintains the attached vertebrae in a desired spacing and orientation with respect to each other.

One of the problems associated with bone fixation systems and methods is the tendency of screws or other fasteners to gradually work loose from the vertebrae after fixation of the bone plate. Slight shock or vibration of the vertebrae, due to walking, climbing stairs, or more vigorous activity by the patient following treatment increases this tendency, jeopardizing the integrity of fixation. Moreover, as the fasteners work loose, the outward protrusion of the heads over other components of the system can be a source of discomfort and present the risk of trauma to adjacent and surrounding soft tissue.

SUMMARY

A bone fixation plate includes a first opening formed in a plate that is configured to receive a first fastener, a second opening formed in the plate that is configured to receives a second fastener, and a retention member that extends into a third opening formed in the plate between the first opening and the second opening, wherein the retention member is elastically deformable between at least three positions.

In other features, at least one of the first opening and the second opening is partially blocked by the retention member in at least one of the two positions. The third opening is in communication with at least one of the first opening and the second opening. The three positions include a rest position, a first toggled position, and a second toggled position.

In yet other features, the retention member blocks at least of a portion of the first opening and the second opening in the rest position. The retention member elastically deforms away from the first opening when the first fastener forces the retention member to the first toggled position. The retention member deforms away from the second opening when the second fastener forces the retention member to the second toggled position.

A system for bone fixation includes a plate including a first aperture, a second aperture, and an opening between the first and the second apertures; a retention member extending into the opening of the plate that is elastically deformable from a rest position to first and second toggled positions; a first screw including a head configured to elastically deform the retention member to the first toggled position; and a second screw including a head configured to elastically deform the retention member to the second toggled position.

In other features, the retention member further includes an arm extending from the plate into the opening and a first projection extending from the arm into the first aperture. A second projection extends from the arm into the second aperture.

In yet other features, the first projection blocks a portion of the first aperture and the second projection blocks a portion of the second aperture when the retention member is in the rest position. The first projection is inside the opening of the plate when the retention member is in the first toggled position. The second projection is inside the opening of the plate when the retention member is in the second toggled position. The first screw forces the first projection away from the first aperture in the first toggled position. The second screw forces the second projection away from the second aperture in the second toggled position.

A method for bone fixation includes the steps of inserting a first screw into a first aperture of a plate to secure the plate to a vertebra, advancing the first screw to elastically deform a retention member formed in an opening of the plate, wherein the opening is in communication with the first aperture, elastically deforming the retention member from a rest position to a first toggled position; and advancing the first screw until the retention member elastically returns to the rest position.

In other features, elastically deforming the retention member from the rest position to the first toggled position includes flexing an arm of the retention member. Advancing the first screw to elastically deform the retention member includes contacting a projection of the retention member with a head of the first screw.

In yet other features, the method further includes the steps of inserting a second screw into a second aperture of the plate, advancing the second screw to elastically deform the retention member formed in the opening of the plate, wherein the opening is in communication with the second aperture, elastically deforming the retention member from the rest position to a second toggled position; and advancing the second screw until the retention member elastically returns to the rest position. The first aperture and the second aperture are partially blocked when the retention member is in the rest position and one of the first and second apertures is partially blocked when the retention member is in one of the first toggled position and the second toggled position.

DETAILED DESCRIPTION

Some fasteners and bone fixation plates may include retention mechanisms that may prevent the screws from working loose from the plate and vertebra. However, many retention mechanisms are cumbersome and difficult to operate during surgical procedures. For example, some plates may have retention mechanisms that include additional hardware and features such as sliding tabs or projections, springs, and the like. The additional hardware adds weight and complexity to the plates and presents potential failure modes such as jammed tabs, broken springs, or other failures from the separate moving parts. The additional hardware may also require activation by the surgeon. That is, the surgeon may be required to find the activation point and twist or press a feature on the screw or plate to activate the retention mechanism. These additional steps require additional time and effort by the surgeon who is already under difficult working conditions such as low light and a confined surgical area.

Accordingly, a bone fixation system and method are provided to decrease weight and complexity while reducing the duration of the surgical procedure. The bone fixation plate of the present disclosure includes an integrated retention mechanism that is formed in the bone fixation plate itself. The retention mechanism includes geometry introduced into the bone fixation plate during the manufacturing process. For example, the geometry may be introduced by forming the retention mechanism out of a mold or cutting with a laser or plasma cutting technique. Thus, the retention mechanism requires no additional hardware on the bone fixation plate. The bone fixation plate of the present disclosure further includes a self-activating retention mechanism that automatically locks when a fastener is inserted to attach the plate to a vertebra.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
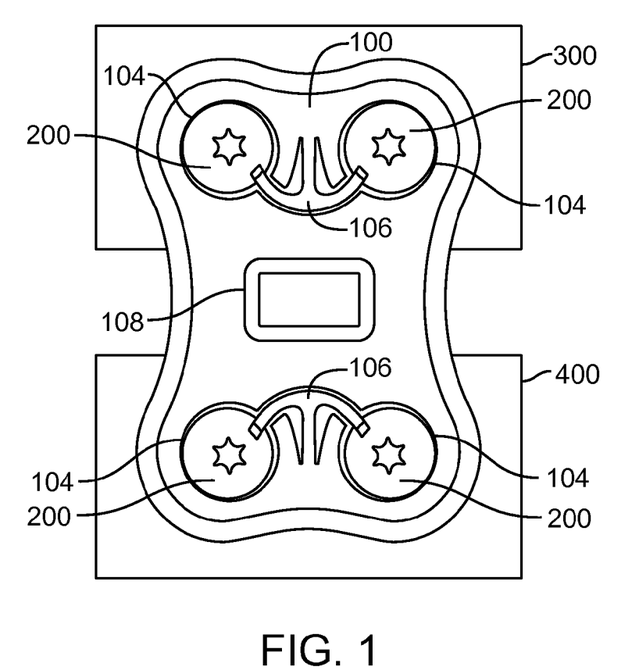
FIG. 1 is an elevational view of a bone fixation system attached to adjacent vertebrae according to the principles of the present disclosure.

Referring now to FIG. 1, a bone fixation plate 100, hereinafter referred to as the "plate," is configured to be attached to a first vertebra 300 and a second vertebra 400 using bone screws 200. The plate 100 may be substantially rectangular and include rounded sides and/or contoured surfaces to facilitate movement of tissue relative to the plate 100 after implantation in a patient. The plate 100 includes apertures 104 formed in corners of the plate 100. The screws 200 pass through the apertures 104 to attach to the vertebrae 300 and 400. Retention mechanisms 106, formed between the apertures 104 in the plate 100, keep the screws 200 from backing out of the vertebrae 300 and 400 after fixation. A window 108 may also be formed in the plate 100 to provide access to the space between the first vertebra 300 and the second vertebra 400. Although the system and method shown herein may be used to fix together two vertebrae, it is understood that the system and method may be applicable to multiple vertebrae in excess of two. For example, the plate 100 may extend beyond the first and/or second vertebra to attach to other adjacent vertebrae and may include additional retention mechanisms disposed between additional pairs of apertures and screws.

Figure 2:
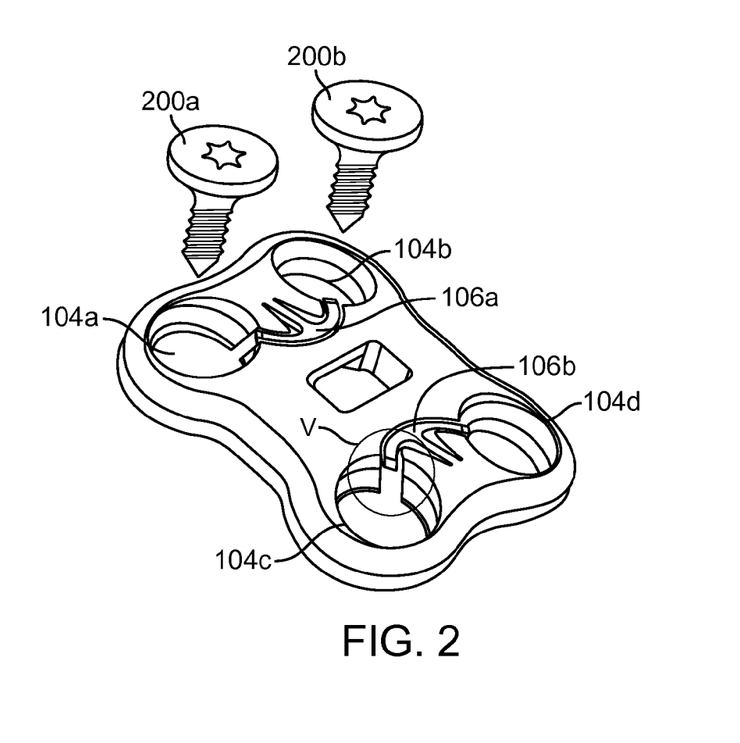
FIG. 2 is an exploded perspective view of the bone fixation system according to the principles of the present disclosure.

Referring now to FIG. 2, a first screw 200a may be inserted through a first aperture 104a and a second screw 200b may be inserted through a second aperture 104b. A first retention mechanism 106a is disposed between the first and second apertures 104a and 104b and is configured to prevent both the first screw 200a and the second screw 200b from backing out of the plate 100 after fixation to the first vertebra 300. In one embodiment, the first retention mechanism 106a may be molded or machined from the material of the plate 100. Thus, the first retention mechanism 106a may be integral and continuous with the plate 100. In other embodiments, the first retention mechanism 106a may be attached to the plate 100 between the apertures 104a and 104b. The first retention mechanism 106a may be attached by welding, snap fit, friction welding, or other forms of attachment.

For simplicity, one retention mechanism and one pair of adjacent apertures are discussed in detail herein. However, it is understood by one in the art that the plate 100 of the present disclosure may include one or more retention mechanisms disposed between any pair of apertures. For example, third and fourth apertures 104c and 104d may be mirror images of the first and second apertures 104a and 104b and configured to receive third and fourth screws, respectively. Similarly, a second retention mechanism 106b may be disposed between the third and fourth apertures 104c and 104d. It may be readily understood by one in the art that the second retention mechanism 106b functions the same as the first retention mechanism 106a with respect to the third and fourth apertures 104c and 104d. Thus, each of the retention mechanisms 106a and 106b may be referred to hereinafter as simply retention mechanism 106. Likewise, each pair of apertures may be referred to hereinafter as simply first and second apertures 104a and 104b.

Figure 3:
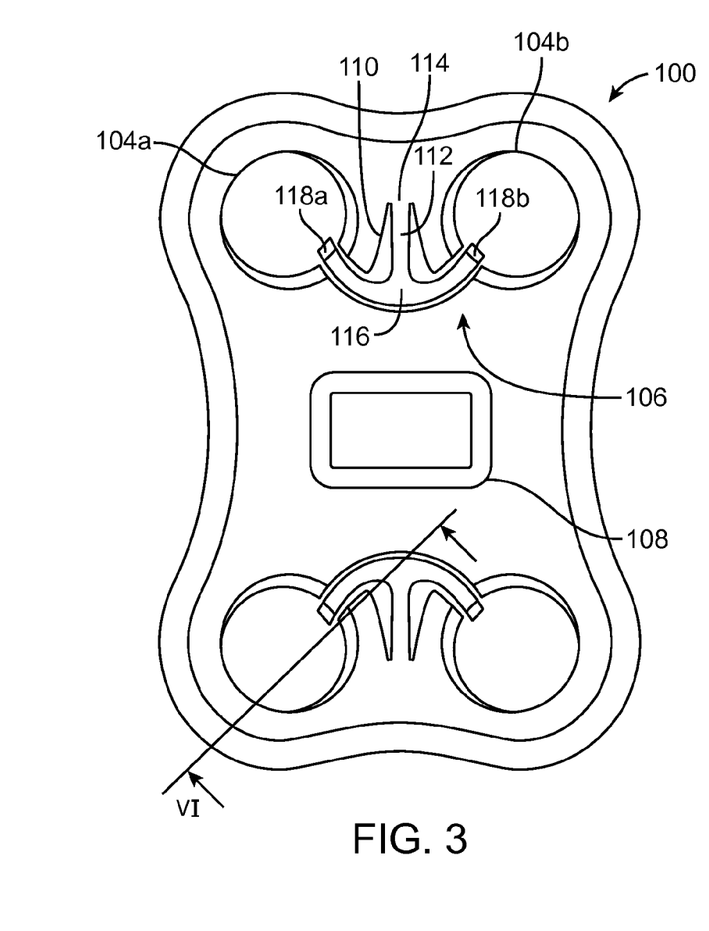
FIG. 3 is a top elevational view of the bone fixation plate according the principles of the present disclosure.

Referring now to FIG. 3, a top view of the plate 100 illustrates additional features of the retention mechanism 106 and apertures 104a and 104b. The first aperture 104a and the second aperture 104b are formed in one end of the plate 100. The first and second apertures 104a and 104b may be substantially circular and configured to receive the bone screws 200a and 200b respectively as shown in FIG. 2. The retention mechanism 106 is disposed in an opening 110 formed between the first and second apertures 104a and 104b. The opening 110 may be irregular-shaped to conform to the geometry of the retention mechanism 106. In one embodiment, the opening 110 may be in communication with both the first aperture 104a and the second aperture 104b. That is, a continuous wall is shared between the first aperture 104a, the second aperture 104b, and the opening 110.

The retention mechanism 106 extends from the plate 100 into the opening 110 and is configured to lock the bone screws 200a and 200b to the plate 100. For example, the retention mechanism 106 may include a flexible arm 112 extending from the plate 100 into the opening 110. The flexible arm 112 may be attached to the plate at a proximal end 114 and include a distal end 116 cantilevered in the opening 110. A first projection 118a extends from the distal end 116 through the opening 110 and towards the first aperture 104a. A second projection 118b extends from the distal end 116 through the opening 110 towards the second aperture 104b. Thus, the retention mechanism 106 may resemble an inverted "T" shaped geometry or a nautical anchor. For example, the first and second projections 118a and 118b (collectively projections 118) may include curvature having a radius approximately equivalent to the length of the arm 112 from the proximal end 114 to the distal end 116.

Figure 4:
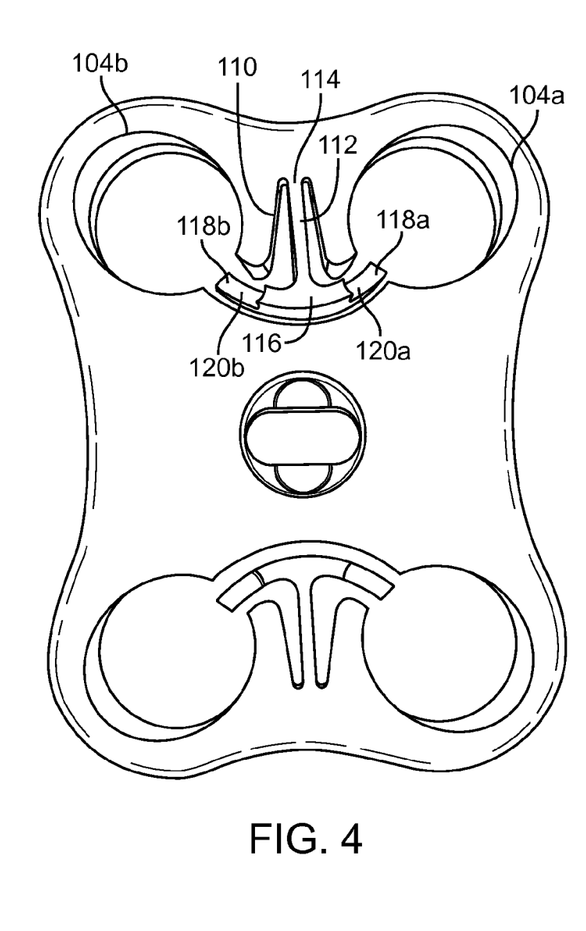
FIG. 4 is a bottom elevational view of the bone fixation plate according to the principles of the present disclosure.

Referring now to FIG. 4, a bottom view of the plate 100 illustrates additional features that enable retention of two bone screws with one retention mechanism 106. Each of the projections 118a and 118b includes a notch 120a and 120b respectively (collectively notches 120), formed at the ends of the projections 118. The notches 120 permit the projections 118 to slide over heads of the screws 200 after fixation to the vertebra 300 as described below with reference to FIGS. 6A-6D and 7A-7E. The notches 120 may be configured to adjust the strength of the retention mechanism 106 by varying the thickness of the projections 118 and/or the arms 112. For example, the notches 120 may decrease the thickness of the retention mechanism 106 and thus increase flexibility. Alternatively, the retention mechanism 106 may be of a uniform thickness that permits the projections 118 to slide over heads of the screws 200.

The retention mechanism 106 is capable of elastically moving, bending, or toggling between at least three distinct positions. In a rest position, as shown in FIGS. 1-5, the arm 112 "rests" substantially equidistant from the first and second apertures 104a and 104b. Both the first projection 118a and the second projection 118b extend partially into the first and second apertures 104a and 104b respectively to retain first and second screws 200a and 200b within the apertures 104a and 104b. From the rest position, the retention mechanism 106 may be toggled to a first toggled position and a second toggled position as discussed below.

Figure 5:
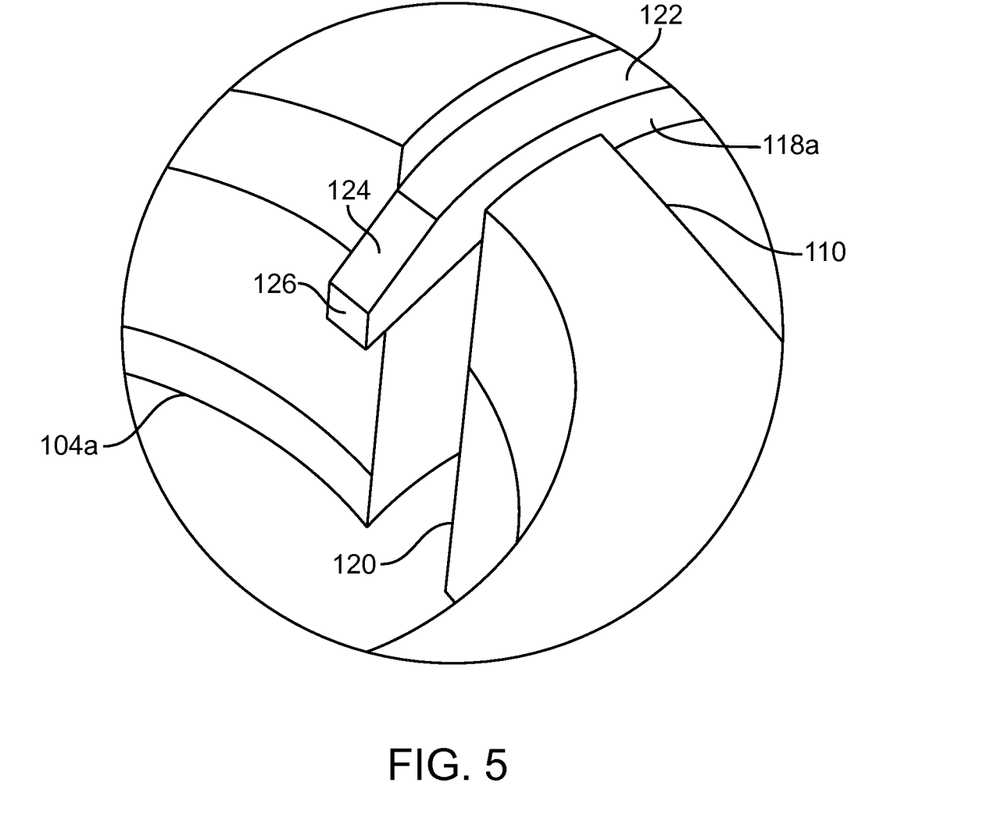
FIG. 5 is a partial perspective view of a retention mechanism in the bone fixation plate of FIG. 2 according to the principles of the present disclosure.

Referring now to FIG. 5, a portion of the retention mechanism 106b of FIG. 2, and more particularly the first projection 118a is shown in greater detail. The first projection 118a extends through a mouth 120 in the opening 110 and into the first aperture 104a. The mouth 120 provides communication between the opening 110 and the aperture 104a. The first projection 118a may include a top surface 122 that substantially conforms to a top surface 123 of the plate 100. The first projection 118a may include a taper 124 that decreases in thickness from the top surface 122 to a tip 126 on the distal end of the first projection 118a. The taper 124 may facilitate engagement with the screw 200 as illustrated in FIGS. 6A-6D.

Figure 6A:
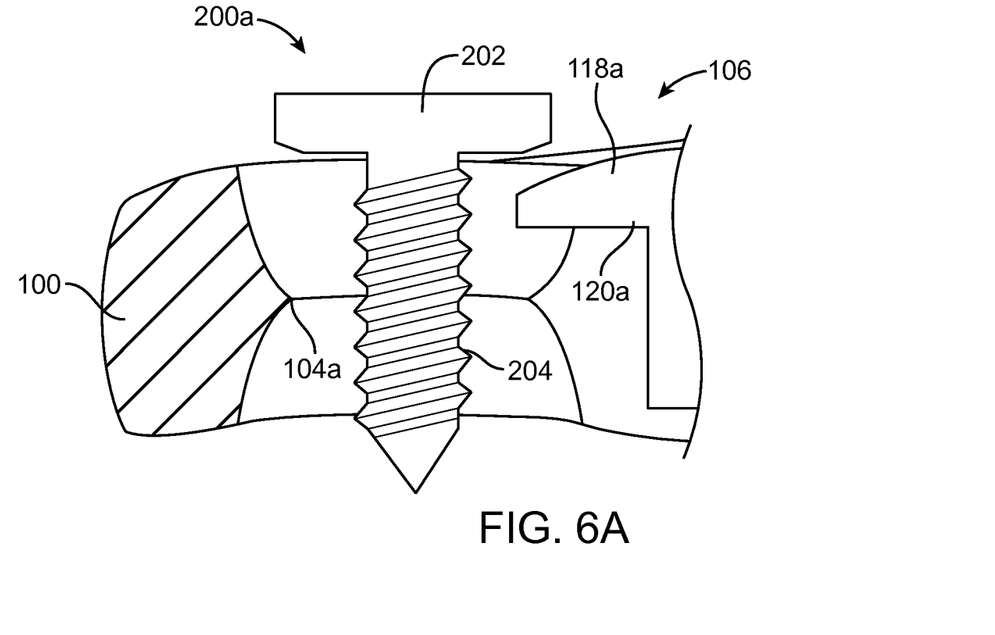
FIGS. 6A-6D are partial cross-sectional views of a portion of the bone fixation plate along line VI of FIG. 3 and a bone screw according to the principles of the present disclosure.
Figure 6B:
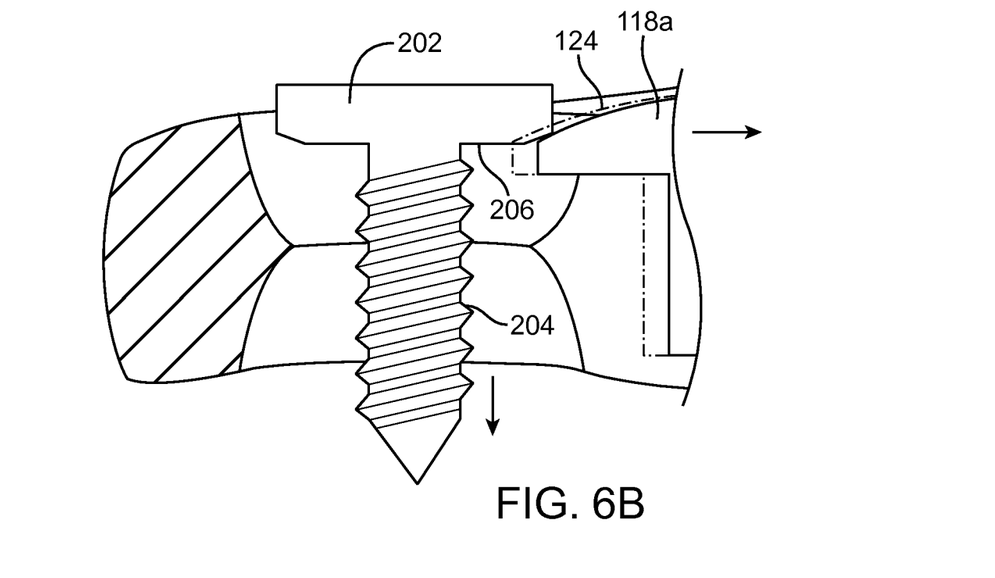

Referring now to FIGS. 6A-6D, engagement between the screw 200 and the retention mechanism 106 are shown in greater detail. The screw 200 includes a head 202 and a threaded shaft 204. The head 202 may be driven by a screwdriver such that the shaft 204 penetrates the vertebra (not shown) to secure the plate 100. In FIG. 6A, the screw 200 is inserted into the first aperture 104a. As the screw 200 advances through the first aperture 104a, a bottom surface 206 of the head 202 moves towards the retention mechanism 106. As the head 202 is driven, the shaft 204 engages more of the vertebra, and the bottom surface 206 begins to contact the taper 124 of the first projection 118a as shown in FIG. 6B. The bottom surface 206 exerts a downward force on the retention mechanism 106. The downward force pushes against the taper 124 which transfers a portion of the downward force to the retention mechanism 106. The flexible arm 112 (not shown) bends due to the force, and the projection 118a begins to move away from the first aperture 104a, as illustrated in detail in FIG. 6B.

Figure 6C:
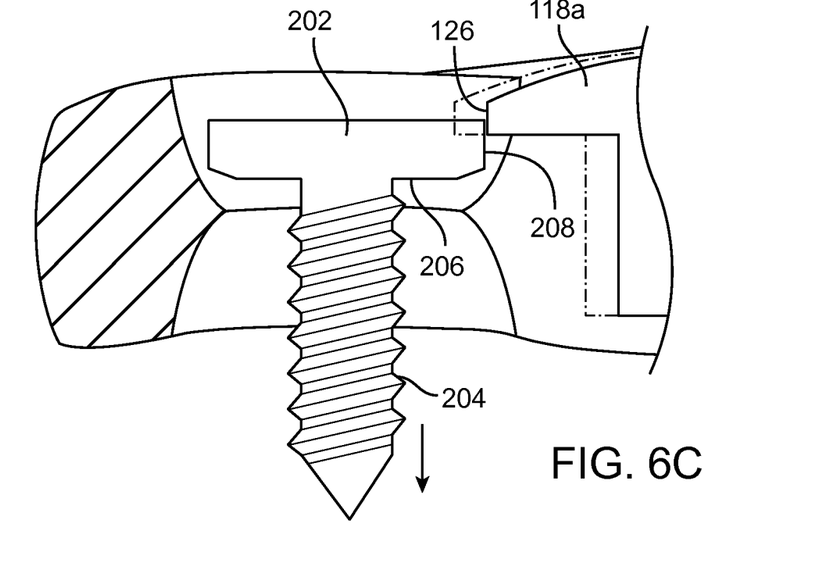
Figure 6D:
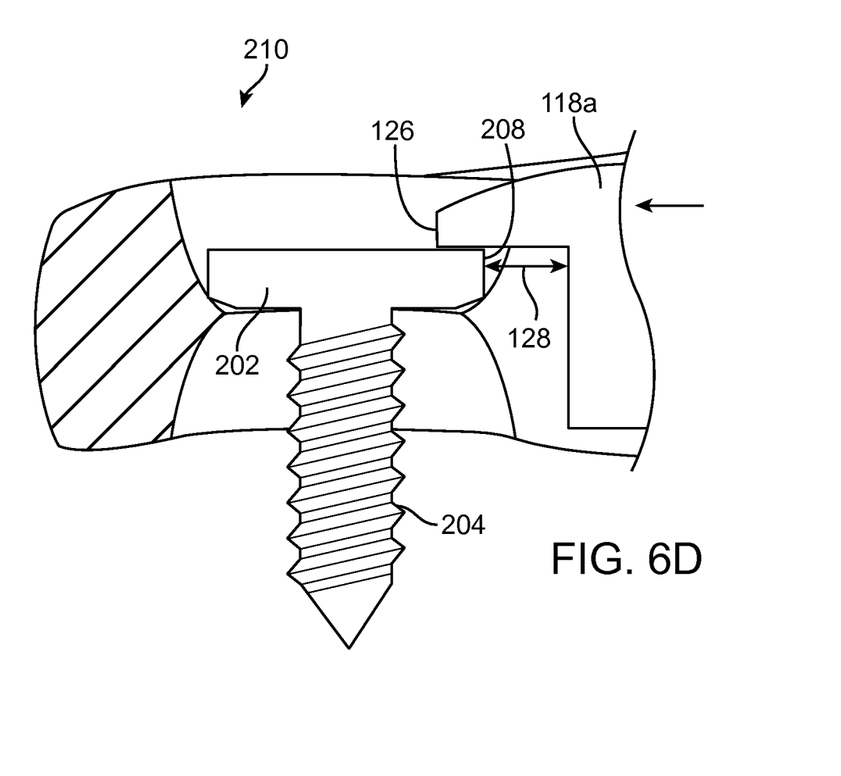

Continuing now with FIG. 6C, as the screw 200 continues to be driven into the vertebra, the bottom surface 206 passes by the taper 124 and a side wall 208 of the head 202 contacts the tip 126 of the projection 118a. At this point, the retention mechanism 106 is in the first toggled position. In a toggled position, the arm 112 of the retention mechanism 106 may be fully bent towards the opposing aperture as will be discussed in detail below. The screw 200 continues to be driven into the vertebra until fully seated in FIG. 6D. Once the screw 200 is fully seated, the retention mechanism 106 returns to the rest position. Now, the tip 126 of the projection 118a extends over a top surface 210 of the head 202 of the screw 200 and the bottom surface 206 may contact a lip 127 in the aperture 104a. Thus, the retention mechanism 106 prevents the screw 200 from backing out from the plate 100. Although the top surface 210 of the screw 200 contacts the projection 118a in FIG. 6D, a gap may remain after the screw 200 attaches to a vertebra. As can be seen in FIG. 6D, a gap 128 may remain between the projection 118a and the side wall 208 of the screw 200 once the retention mechanism 106 has returned to the rest position. The gap 128 permits the retention mechanism 106 to bend towards the first aperture 104a when the second screw 200b is inserted into the second aperture 104b as discussed below with reference to FIGS. 7A-7E.

Figure 7A:
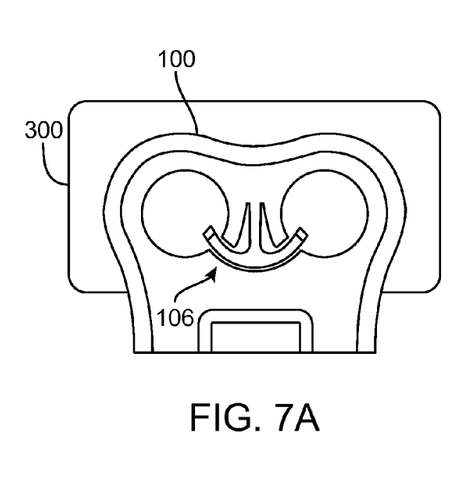
FIGS. 7A-7E are partial top elevational views of one end of the bone fixation system as the end is attached to one of the vertebrae.
Figure 7B:
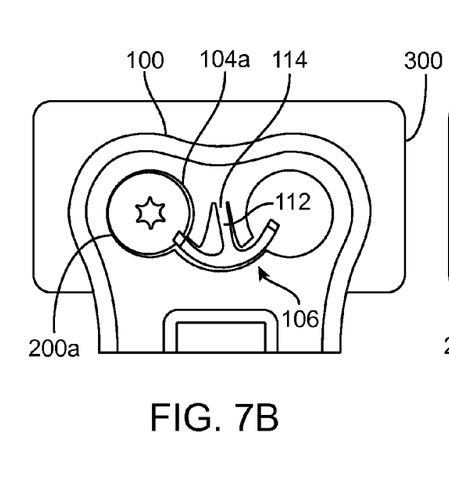
Figure 7C:
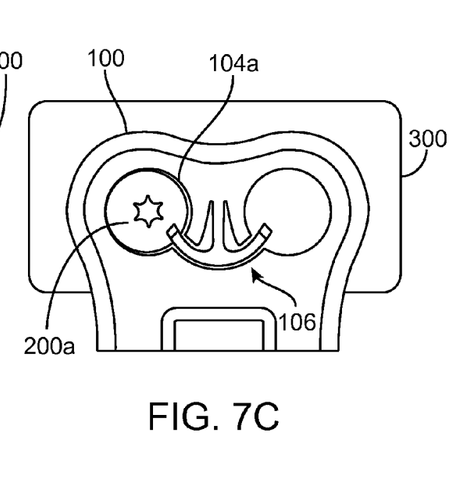

Referring now to FIGS. 7A-7E, the bone fixation system and method are shown in greater detail by a series of partial top views. In FIG. 7A, a first half of the plate 100 is shown positioned over the first vertebra 300. The retention mechanism 106 is in the rest position with no screws in place. In FIG. 7B, the first screw 200a is inserted into the first aperture 104a and driven into the vertebra 300. As described with respect to FIGS. 6B-C, the bottom surface 206 of the screw 200a contacts the taper 124 causing the retention mechanism 106 to bend about the proximal end 114 of the arm 112. The arm 112 elastically bends to the first toggled position before the first screw 200a is fully seated in the first aperture 104a. In FIG. 7C, the first screw 200a is fully seated in the first aperture 104a. The retention mechanism 106 returns to the rest position to prevent the first screw 200a from backing away from the plate 100. The tip 126 of the projection 118a extends over the top surface 210 of the screw head 202, as shown in FIG. 6D. Thus, the screw head 202 is locked between the projection 118a and the lip 127.

Figure 7D:
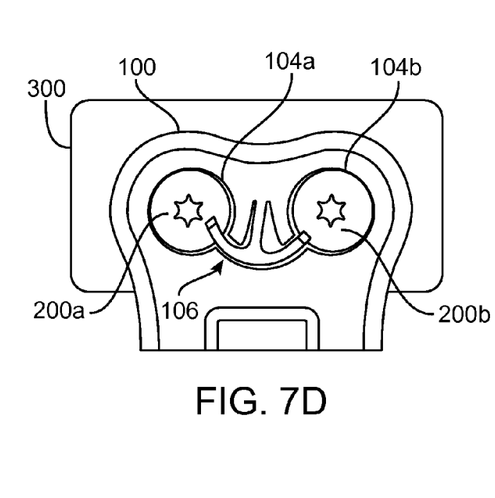
Figure 7E:
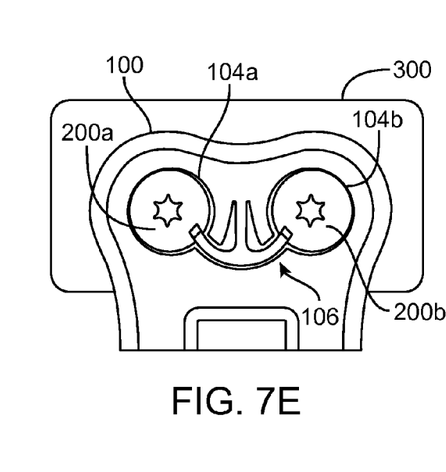

Referring now to FIG. 7D, the second screw 200b is inserted into the second aperture 104b and driven into the vertebra 300. As described with respect to FIGS. 6B-C, the bottom surface 206 of the screw 200b contacts the taper 124 on the distal end of the projection 118b causing the retention mechanism 106 to bend about the proximal end 114 of the arm 112. The arm 112 elastically bends to the second toggled position before the second screw 200b is fully seated in the second aperture 104b. In FIG. 7E, the second screw 200a is fully seated in the second aperture 104b. The retention mechanism 106 returns to the rest position to prevent the second screw 200b from backing away from the plate 100. The tip 126 of the projection 118b extends over the top surface 210 of the screw head 202 of the second screw 202b.

Thus, the screw head 202 is locked between the projection 118b and a corresponding lip 127 of the second aperture 104b.

Figure 8:
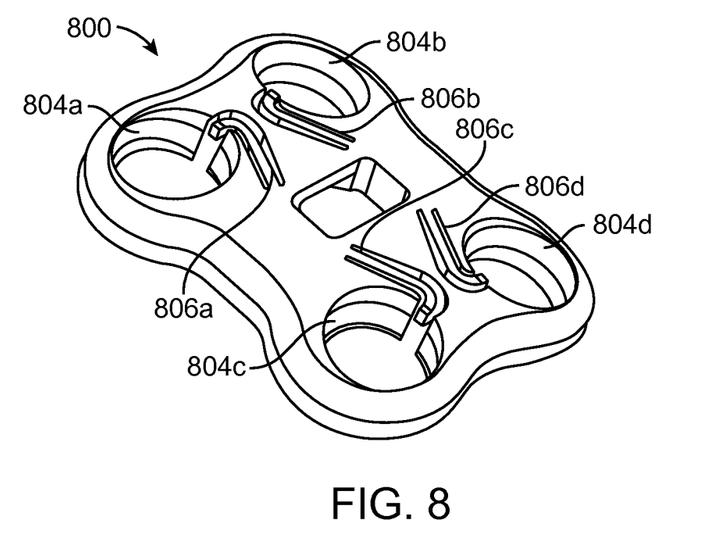
FIG. 8 is a perspective view of another bone fixation plate according to the principles of the present disclosure.
Figure 9:
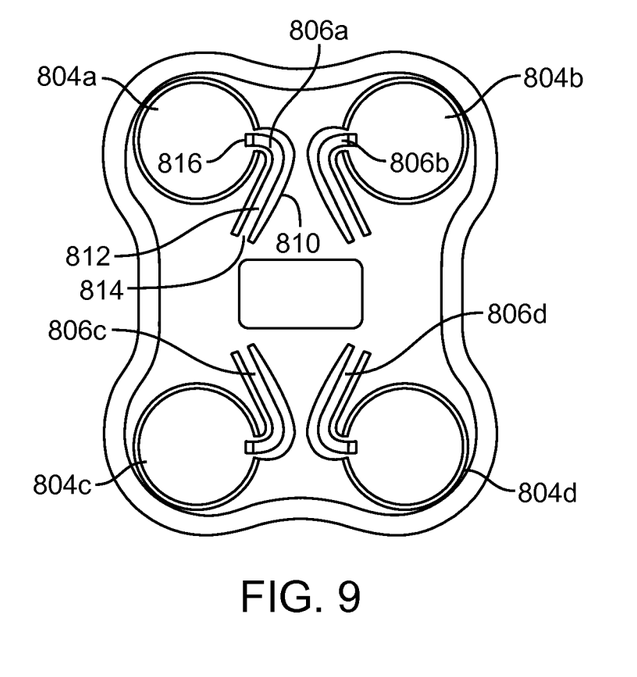
FIG. 9 is a top view of another bone fixation plate according to the principles of the present disclosure.

FIGS. 8 and 9 illustrate another embodiment of a bone fixation plate 800 that includes separate retention mechanisms 806a-d (collectively retention mechanisms 806) for each aperture 804a-d (collectively apertures 804). For example, a first retention mechanism 806a is disposed between first and second apertures 804a and 804b and is configured to prevent a first screw (not shown) in the first aperture 804a from backing out of the plate 800 after fixation to a vertebra. The first retention mechanism 806a may be molded or machined from the material of the plate 800. Thus, the first retention mechanism 806a may be integral and continuous with the plate 800. In other embodiments, the first retention mechanism 806a may be attached to the plate 100 between the apertures 804a and 804b. The first retention mechanism 806a may be attached by welding, snap fit, friction welding, or other forms of attachment. A second retention mechanism 806b is disposed between the second aperture 804b and the first retention mechanism 806a and is configured to prevent a second screw (not shown) in the second aperture 804b from backing out of the plate 800 after fixation to the vertebra.

For simplicity, two retention mechanisms and one pair of adjacent apertures are discussed in detail herein. However, it is understood by one in the art that the plate 800 of the present disclosure may include two retention mechanisms disposed between any pair of apertures. For example, third and fourth apertures 804c and 804d may be mirror images of the first and second apertures 804a and 804b and configured to receive third and fourth screws, respectively. Similarly, a third retention mechanism 806c, may be disposed between the third and fourth apertures 804c and 804d and a fourth retention mechanism 806d may be disposed between the fourth aperture 804d and the third retention mechanism 806c.

Referring now to FIG. 9, a top view of the plate 800 illustrates additional features of the retention mechanism 806 and apertures 804a and 804b. The first aperture 804a and the second aperture 804b are formed in one end of the plate 100. The first and second apertures 804a and 804b may be substantially circular and configured to receive the bone screws 200a and 200b respectively (not shown), similar to apertures 104a and 104b as shown in FIG. 2. Each retention mechanism 806 is disposed in a separate opening 810 formed around each retention mechanism 806. The openings 810 may be irregular-shaped to conform to the geometry of the retention mechanism 806. In one embodiment, each opening 810 may be in communication with a neighboring aperture 804. That is, a continuous wall is shared between one aperture, such as aperture 804a and one opening 810.

Each retention mechanism 806 extends from the plate 800 into the opening 810 and is configured to lock one bone screw to the plate 800. The retention mechanism 806 includes a flexible arm 812 extending from the plate 800 into the opening 810. The flexible arm 812 may be attached to the plate at a proximal end 814 and include a distal end 816 cantilevered in the opening 810. A projection 818 extends from the distal end 816 through the opening 808 and towards the aperture 804. Thus in the present embodiment, the retention mechanism 806 may resemble a "J" shaped geometry or a cane. For example, the projection 818 may include curvature having a radius equivalent to the length of the arm 812 from the proximal end 814 to the distal end 816.

The retention mechanisms 806 function similar to the retention mechanism 106 as depicted in FIGS. 6A-6D. That is, each retention mechanism 806 includes a taper on the projection 818 that comes in contact with a bottom surface of a screw when the screw is driven into a vertebra. As the screw is driven further into the vertebra, the retention mechanism 806 contacts an outer wall of the head of the screw and moves from a rest position to a toggled position. However, in the present embodiment, each retention mechanism 806 locks one screw rather than two screws as retention mechanism 106. Thus, the retention mechanism 806 in the present example may be toggled between the rest position as depicted in FIGS. 8 and 9 and one toggled position similar to the first toggled position of the retention mechanism 106.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A bone fixation plate comprising:
a first opening formed in a plate that is configured to receive a first fastener;
a second opening formed in the plate that is configured to receives a second fastener; and
a retention member including:
a first arm that extends into a third opening formed in the plate between the first opening and the second opening,
a first projection extending from a free end of the first arm towards the first aperture, and
a second projection extending from the free end of the first arm towards the second aperture,
each projection having a radius of curvature equivalent to a length of the first arm and forming together with the first arm a "T" shaped geometry,
wherein the retention member is elastically deformable between at least three positions,
wherein the third opening is in communication with at least one of the first opening and the second opening and the first, second, and third openings share a continuous wall extending completely through the plate and forming a "T" shaped geometry surrounding the retention member.

2. The bone fixation plate of claim 1, wherein at least one of the first opening and the second opening is partially blocked by at least one of the first and second projections of the retention member in at least one of the two positions.

3. The bone fixation plate of claim 1, wherein the three positions include a rest position, a first toggled position, and a second toggled position.

4. The bone fixation plate of claim 3, wherein the first projection blocks at least of a portion of the first opening and the second projection blocks at least a portion of the second opening when the retention member is in the rest position.

5. The bone fixation plate of claim 3, wherein the retention member elastically deforms away from the first opening when the first fastener forces the retention member to the first toggled position.

6. The bone fixation plate of claim 3, wherein the retention member deforms away from the second opening when the second fastener forces the retention member to the second toggled position.

7. A system for bone fixation comprising:
a plate including a first aperture, a second aperture, and an opening between the first and the second apertures;
a retention member including:
- a first arm extending into the opening of the plate that is elastically deformable from a rest position to first and second toggled positions,
- a first projection extending from a free end of the first arm towards the first aperture, and
- a second projection extending from the free end of the first arm towards the second aperture,
- each projection having a radius of curvature equivalent to a length of the first arm and forming together with the first arm a "T" shaped geometry;

a first screw including a head configured to elastically deform the retention member to the first toggled position; and
a second screw including a head configured to elastically deform the retention member to the second toggled position,
wherein the opening is in communication with at least one of the first aperture and the second aperture and shares a continuous wall with at least one of the first aperture and the second aperture that extends completely through the plate and that forms a "T" shaped geometry surrounding the retention member.

8. The system of claim 7, wherein the first projection blocks a portion of the first aperture and the second projection blocks a portion of the second aperture when the retention member is in the rest position.

9. The system of claim 7, wherein the first projection is inside the opening of the plate when the retention member is in the first toggled position.

10. The system of claim 7, wherein the second projection is inside the opening of the plate when the retention member is in the second toggled position.

11. The system of claim 7, wherein the first screw forces the first projection away from the first aperture in the first toggled position.

12. The system of claim 7, wherein the second screw forces the second projection away from the second aperture in the second toggled position.

* * * * *